United States Patent
Mehrpouyan et al.

(10) Patent No.: US 12,000,836 B2
(45) Date of Patent: Jun. 4, 2024

(54) METHODS FOR QUANTITATING EXTRA-CELLULAR VESICLE SURFACE MARKERS, AND COMPOSITIONS FOR PRACTICING THE SAME

(71) Applicant: Becton, Dickinson and Company, Franklin Lakes, NJ (US)

(72) Inventors: Majid Mehrpouyan, Gilroy, CA (US); Oleg Guryev, San Jose, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 648 days.

(21) Appl. No.: 17/126,583

(22) Filed: Dec. 18, 2020

(65) Prior Publication Data
US 2021/0190790 A1    Jun. 24, 2021

Related U.S. Application Data

(60) Provisional application No. 62/951,968, filed on Dec. 20, 2019.

(51) Int. Cl.
*G01N 33/58* (2006.01)
*G01N 21/64* (2006.01)

(52) U.S. Cl.
CPC ....... *G01N 33/586* (2013.01); *G01N 21/6428* (2013.01); *G01N 21/6486* (2013.01); *G01N 33/582* (2013.01); *G01N 2496/00* (2013.01)

(58) Field of Classification Search
CPC .... G01N 33/58; G01N 33/582; G01N 33/586; G01N 33/48; G01N 33/92; G01N 2496/00; G01N 21/64; G01N 21/6428; G01N 21/6486; G01N 15/00; G01N 15/10; G01N 15/14
USPC ............. 436/13, 63, 71, 164, 172, 501, 536; 422/82.08; 435/7.1, 7.2
See application file for complete search history.

(56) References Cited

U.S. PATENT DOCUMENTS

| | | | |
|---|---|---|---|
| 2017/0045451 A1* | 2/2017 | Nolan | G01N 21/6428 |
| 2017/0341049 A1 | 11/2017 | Guryev et al. | |
| 2018/0299452 A1* | 10/2018 | Nagai | G01N 33/57488 |
| 2022/0305405 A1* | 9/2022 | Okeoma | B01D 15/1871 |

FOREIGN PATENT DOCUMENTS

| | | |
|---|---|---|
| WO | WO2017027622 A1 | 2/2017 |
| WO | WO2018126043 A1 | 7/2018 |

OTHER PUBLICATIONS

Stoner et al. Cytometry, Part A, vol. 89A, Oct. 20, 2015, pp. 196-206.*
Vagida et al. Biochemistry (Moscow), vol. 81, No. 4, Feb. 7, 2016, pp. 382-391.*
Erdbrügger, et al., "Imaging flow cytometry elucidates limitations of microparticle analysis by conventional flow cytometry: Microparticle Detection by Imaging Flow Cytometry", Cytometry A, vol. 85, No. 9, 5, 2014, pp. 756-770.
Guryev, et al., "PS04.03-Quantification of extra-cellular vesicle surface markers with MESF liposomes", Annual Meeting ISEV 2020, 2020, 2 Pages.
Simonsen, "A liposome-based size calibration method for measuring microvesicles by flow cytometry", Journal of Thrombosis and Haemostasis, vol. 14, No. 1, 2015, pp. 186-190.
Al Nedawi, et al. "Intercellular transfer of the oncogenic receptor EGFRvIII by microvesicles derived from tumour cells", Nature Cell Biology 10(5):619-24, Jun. 2008.
De Rond, et al. "Comparison of Generic Fluorescent Markers for Detection of Extracellular Vesicles by Flow Cytometry", Clinical Chemistry, vol. 64, Issue 4, Apr. 1, 2018, pp. 680-689.
El Andaloussi, et al., "Extracellular vesicles: biology and emerging therapeutic opportunities", Nature Reviews Drug Discovery vol. 12, pp. 347-357 (2013).
Guryev, et al. "PS04.03-Quantification of extra-cellular vesicle surface markers with MESF liposomes, Annual Meeting ISEV 2020", Jul. 20, 2020, 1 page, Abstract only.
Kowal, et al. "Biogenesis and secretion of exosomes", Current Opinion in Cell Biology 29C(1):116-125, Jun. 22, 2014.
Maas, et al. "Possibilities and limitations of current technologies for quantification of biological extracellular vesicles and synthetic mimics", Journal of Controlled Release, Dec. 30, 2014, vol. 200, pp. 87-96.
Poon, et a;. "Self-assembled nanoscale coordination polymers carrying oxaliplatin and gemcitabine for synergistic combination therapy of pancreatic cancer", J Control Release. Mar. 10, 2015; 201: 90-99.
Saman, et al. "Exosome-associated Tau Is Secreted in Tauopathy Modelsand Is Selectively Phosphorylated in Cerebrospinal Fluid inEarly Alzheimer Disease", J Biol Chem. Feb. 3, 2012;287(6):3842-9.
Shao, et al. "Protein typing of circulating microvesicles allows real-time monitoring of glioblastoma therapy", Nat Med . Dec. 2012;18(12):1835-40.

(Continued)

*Primary Examiner* — Maureen Wallenhorst
(74) *Attorney, Agent, or Firm* — Darya C. Cheng; Bret E. Field; BOZICEVIC, FIELD & FRANCIS LLP

(57) ABSTRACT

Methods of quantitating extra-cellular vesicle surface markers are provided. Aspects of the methods include comparing: a mean fluorescence intensity of a surface marker of interest (surface marker MFI) of a labeled extra-cellular vesicle (EV) sample with a calibration plot obtained from a liposome calibration composition to quantitate the surface marker on extra-cellular vesicles of the EV sample. Also provided are compositions that find use in practicing embodiments of the invention.

14 Claims, 6 Drawing Sheets

(56) References Cited

OTHER PUBLICATIONS

Simonsen "A liposome-based size calibration method for measuring microvesicles by flow cytometry", Journal of Thrombosis and Haemostasis : JTH, Jan. 4, 2016, pp. 186-190.

Skog, et al., "Glioblastoma microvesicles transport RNA and protein that promote tumor growth and provide diagnostic biomarkers" Nat Cell Biol. Dec. 2008; 10(12): 1470-1476.

Mizrahi, et al. "Quantitative flow cytometry: concerns and recommendations in clinic and research", Cytometry Part B Clinical Cytometry, Mar. 2018, vol. 94, No. 2, pp. 211-218.

Welsh, et al. "Extracellular vesicle flow cytometry analysis and standardization, Frontiers in Cell and Developmental Biology", Aug. 30, 2017, vol. 5, Article No. 78, Internal pp. 1-7.

* cited by examiner

METHODS FOR QUANTITATING EXTRA-CELLULAR VESICLE SURFACE MARKERS, AND COMPOSITIONS FOR PRACTICING THE SAME

CROSS-REFERENCE TO RELATED APPLICATION

Pursuant to 35 U.S.C. § 119(e), this application claims priority to the filing dates of U.S. Provisional Patent Application Ser. No. 62/951,968 filed Dec. 20, 2019; the disclosure of which applications is incorporated herein by reference.

INTRODUCTION

Extra-cellular Vesicles (also known in the art as EV particles) are lipid membrane-enclosed vesicles released by cells and present in body fluids. EVs are heterogeneous in composition and size, ranging from 50-1000 nm in diameter (Nat. Rev. Drug Discov. 12 (5) (2013) 347-357; Curr. Opin. Cell Biol. 29C (2014) 116-125). EVs originate from their donor cell as a result of outward budding of the plasma membrane. Multiple reports have demonstrated that EVs play an important role in the pathophysiological process, such as immune responses and tumor growth (Nat. Cell Biol. 10 (12) (2008) 1470-1476; Nat. Cell Biol. 10 (5) (2008) 619-624). Accordingly, EVs present in body fluids have been employed as biomarkers for diagnosis and monitoring disease (J. Biol. Chem. 277 (6) 2012) 3842-3849). Since tumor-derived EVs are released in easily accessible body fluid, such as blood or urine (Nat. Cell Biol. 10 (12) (2008) 1470-1476; Nat. Med. 18 (12) (2012) 1835-1840), analysis of these EVs for disease monitoring may circumvent biopsies.

Flow cytometry has been used extensively for analysis of EV particles stained with fluorescent antibodies directed to the known cell surface markers. Commercial flow cytometers measure only the relative fluorescence of surface markers in the form of Mean (or Median) Fluorescent Intensities (MFI). Changes in instrument setup, service, or replacement, as well as changes in fluorescent antibodies from different vendors, all impact the relative MFI values for the same sample. This impact limits the use of MFI values for comparison of data acquired over time in different labs and among different instruments.

Even though EVs are increasingly recognized as important biological and therapeutic entities, standardization methods for their analysis are still lacking. Currently employed strategies for analysis of EVs are outlined below:
  Quantitation of EV particles in terms of counting or enumeration of EV particles but not surface markers thereof, e.g., via enumeration with Nanoparticle Tracking Analysis (NTA), high-resolution flow cytometry and Trucount beads (J. Control. Release 200 (2015) 87-96);
  Use of fluorescent dyes that are generic dyes that either integrate into the lipid bilayer or stain any phospholipid membrane with no specificity, such as such as Di-8-ANEPPS, PKH67 or Annexin (Clin. Chem. 64 (4) (2018) 680-689), where such generic markers provide no estimation of the EV surface markers stained with fluorescent antibodies; and
  Staining of EVs with fluorescent antibodies for the identification of the EV surface markers (e.g., CD61-APC, EpCAM-APC), without quantitation thereof.

However, quantitation of the surface markers in terms of the number of molecules or the number of antibodies bound per specific marker has remained one of the largest challenges in the EV research field.

SUMMARY

Methods of quantitating extra-cellular vesicle surface markers are provided. Aspects of the methods include comparing: a mean fluorescence intensity of a surface marker of interest (surface marker MFI) of a labeled extra-cellular vesicle (EV) sample with a calibration plot obtained from a liposome calibration composition to quantitate the surface marker on extra-cellular vesicles of the EV sample. Also provided are compositions that find use in practicing embodiments of the invention.

In one embodiment, a liposome calibration composition made up of a series of fluorescently labeled liposomes with a known number of fluorophores attached to their surfaces is provided. Where desired, the known number for the fluorophores may be expressed in the units known as Molecules of Equivalents Soluble Fluorochrome (MESF). The plot of known number of fluorophore (or MESF) vs. the fluorescent intensity of the liposomes provides a standard curve (i.e., a calibration plot), from which the fluorescent intensity (MFI value) of a stained EV sample can be converted to the number of fluorophores bound to the surface of the EV particles (or MESF value). By this approach, the MFI values are converted to standardized MESF values number of fluorophores (or MESF values) that become independent of instrument variation among different labs, resulting in further improvement of inter-laboratory standardization.

BRIEF DESCRIPTION OF THE FIGURES

FIG. 1A is a schematic representation of liposomes labeled with various numbers of PE fluorochromes. FIG. 1B is a schematic analysis of PE-liposomes in SSC vs. PE fluorescence. FIG. 1C provides a standard curve generated by plotting the MESF values of PE Quantibrite Beads vs. their PE MFI values for MESF assignment to the labeled liposomes of the same color.

FIG. 2A provides size determination of liposome by Dynamic Light Scattering (DLS) analysis. FIG. 2B provides flow cytometry analysis of FITC-labeled liposome on a BD FACS Aria Fusion flow cytometer (Becton, Dickinson and Company). FIG. 2C provides FITC-labeled Liposome analysis after sorting in a FACS Aria Fusion flow cytometer.

FIG. 3A provides flow cytometry analysis of FITC-labeled liposomes on a BD FACS Aria Fusion before sorting. FIG. 3B provides FITC-labeled liposome calibrators generated after sorting in FACS Aria Fusion flow cytometer. The data demonstrates that liposome calibrators labeled with fluorophore can be generated.

DETAILED DESCRIPTION

Figure 1A:
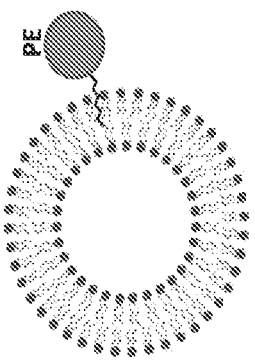
FIGS. 1A to 1C illustrates PE labeled Liposomes as Calibrators.
Figure 1A:
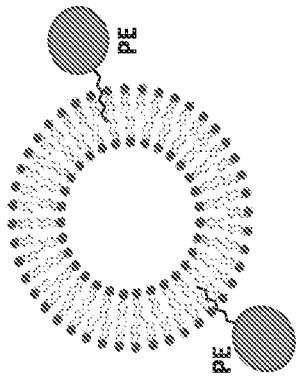
Figure 1A:
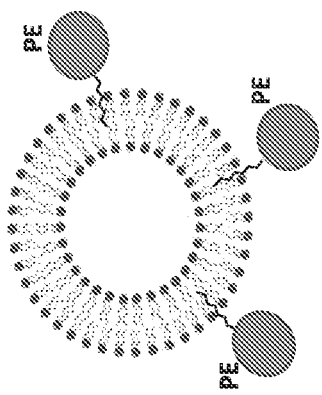
Figure 1A:
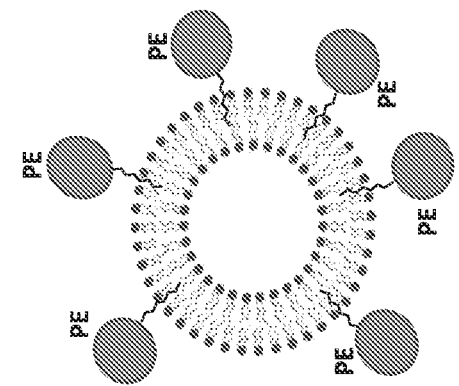

Methods of quantitating extra-cellular vesicle surface markers are provided. Aspects of the methods include comparing: a mean fluorescence intensity of a surface marker of interest (surface marker MFI) of a labeled extra-cellular vesicle (EV) sample with a calibration plot obtained from a liposome calibration composition to quantitate the surface marker on extra-cellular vesicles of the EV sample. Also provided are compositions that find use in practicing embodiments of the invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Methods for Quantitating Extra-Cellular Vesicle Surface Markers

As summarized above, aspects of the present disclosure include methods of quantitating one or more surface markers on extra-cellular vesicles in a sample. As such, aspects of the invention include methods of quantitating one or more extracellular vesicle surface markers (i.e., EV surface marker) in an extra-cellular vesicle containing sample (i.e., EV sample). In some instances, the methods are methods of quantitating a single EV surface marker. In yet other instances, the methods are methods of quantitating two or more distinct EV surface markers (where distinct EV surface markers are molecules that differ from each other in terms of molecular formula, e.g., distinct proteins that have different amino acid sequences). While the number of distinct EV surface markers that are quantitated in such embodiments may vary, in some instances the number of distinct EV surface markers ranges from 2 to 10, such as 2 to 8, e.g., 3 to 5.

As the methods are methods of quantitating one or more EV surface markers, they are methods of obtaining at least an estimation of the amount of a given marker on the surface of EVs in an EV sample, e.g., in the form of at least an estimation of the number of molecules of a given marker that are on the surface of EVs in an EV sample. The quantitation that is obtained using embodiments of the methods may be an average for a number of, including all of, the EVs in the EV sample. As such, the quantitation of a given EV surface marker that is obtained by methods of the invention differs from the mean fluorescence intensity (MFI) obtained for that marker, since mean fluorescence intensity is not a quantitative representation for the marker but instead a relative representation for that marker. The quantitation can be provided in any convenient format, e.g., in terms of number of molecules of a given marker, in terms of the number of fluorophores bound to the surface of EV particles (e.g., as molecules of equivalents soluble fluorochrome or MESF), and the like.

The EV sample for which one or more surface markers are quantified in accordance with the invention may vary, where EV samples are samples that contain EVs of interest. Examples of EV samples include, but are not limited to biological samples, such as a biological fluids, such as but not limited to: urine, blood, plasma, serum, saliva, semen, stool, sputum, cerebral spinal fluid, tears, mucus, sperm, amniotic fluid or the like.

In practicing embodiments of the methods, a mean fluorescence intensity of the surface marker(s) of interest obtained from the EV sample is compared with a calibration plot obtained from a liposome calibration composition, e.g., as described in greater detail below. The mean fluorescence intensity of the surface marker (i.e., surface marker MFI)

that is employed in methods of the invention is one that has been obtained by flow cytometrically analyzing a labeled EV sample. The labeled EV sample is an EV sample that has been labeled with a surface marker label, where the surface marker label includes a specific binding member for the surface marker to be quantified and a fluorophore. Any convenient protocol for flow cytometrically analyzing a labeled EV sample to obtain the surface marker MFI may be employed. In some instances, the surface marker MFI is the median or geometric mean, where the particular MFI that is employed may be chosen based on the nature of the histogram from which it is derived. In some instances, the MFI is obtained using a commercially available program, e.g., FlowJo™ Software flow data analysis software (Becton, Dickinson and Company).

In some instances, methods include preparing the labeled EV sample and obtaining the MFI for the surface marker thereof. The labeled EV sample may be prepared using any convenient protocol. In some instances, the EV sample is combined with a suitable amount of surface marker label that specifically binds to the surface marker to be quantified under conditions sufficient for the surface marker label to bind to the surface of interest and thereby produce the labeled EV sample. As stated above, the surface marker label includes a specific binding member for the surface marker of interest and a fluorescent label.

The specific binding member of the surface marker label specifically binds to the surface marker, such that the specific binding member and the surface marker have affinity for each other. The affinity between the specific binding member and the surface marker may vary, where in some instances they may specifically bind to each other in a binding complex that is characterized by a KD (dissociation constant) of 10-5 M or less, 10-6 M or less, 10-7 M or less, 10-8 M or less, 10-9 M or less, 10-10 M or less, 10-11 M or less, 10-12 M or less, 10-13 M or less, 10-14 M or less, or 10-15 M or less. Any suitable surface marker binding moiety may be employed as the specific binding member, such as protein binding moieties, antibodies or fragments thereof, aptamers, small molecules, ligands, peptides, oligonucleotides, etc., or any combination thereof. For example, a specific binding member can comprise an antibody, for example, an antibody specific for a surface marker (e.g., receptor) on an extracellular vesicle. The antibody can be a full-length (i.e., naturally occurring or formed by normal immunoglobulin gene fragment recombinant processes) immunoglobulin molecule (e.g., an IgG antibody) or an immunologically active (i.e., specifically binding) portion of an immunoglobulin molecule, like an antibody fragment. The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins").

In addition to the specific binding member, the surface marker label further includes a fluorophore. Fluorophores of interest may include, but are not limited to, dyes suitable for use in analytical applications (e.g., flow cytometry, imaging, etc.). A large number of dyes are commercially available from a variety of sources. For example, the fluorophore may be 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin (PE); PE-Cy7, o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; carotenoid-protein complexes, such as peridinin-chlorophyll proteins (PerCP); allophycocyanin (APC); or combinations thereof.

In some instances, the fluorophore of the surface marker label is polymeric dye. Polymeric dyes of interest include, but are not limited to, those dyes described by Gaylord et al. in U.S. Publication Nos. 20040142344, 20080293164, 20080064042, 20100136702, 20110256549, 20110257374, 20120028828, 20120252986, 20130190193, 20160264737, 20160266131, 20180231530, 20180009990, 20180009989, and 20180163054, the disclosures of which are herein incorporated by reference in their entirety; and Gaylord et al., *J. Am. Chem. Soc.*, 2001, 123 (26), pp 6417-6418; Feng et al., *Chem. Soc. Rev.*, 2010, 39, 2411-2419; and Traina et al., *J. Am. Chem. Soc.*, 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorb light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multi-chromophores. The term "water-soluble group" refers to a functional group that is well solvated in aqueous environments and that imparts improved water solubility to the molecules to which it is attached. In some embodiments, a WSG increases the solubility of the multi-chromophore in a predominantly aqueous solution (e.g., as described herein), as compared to a multi-chromophore which lacks the WSG. The water-soluble groups may be any convenient hydrophilic group that is well solvated in aqueous environments. In some cases, the hydrophilic water-soluble group is charged, e.g., positively or negatively charged. In certain cases, the hydrophilic water-soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula —(CH$_2$—CH$_2$—O—)$_n$—, or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky, "Functionalized poly(ethylene glycol) for preparation of biologically relevant conjugates", *Bioconjugate Chemistry* 1995, 6(2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3$', Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{ZZ}$, and R$^{ZZ}$ and R$^{YY}$ are independently selected from H and C$_{1-3}$ alkyl.

The polymeric dye may have any convenient length. In some cases, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments.

The polymeric dyes may be of any convenient molecular weight (MW). In some cases, the MW of the polymeric dye may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In certain embodiments, the polymeric dye has an average molecular weight of 70,000.

In certain instances, the polymeric dye includes the following structure:

where CP$_1$, CP$_2$, CP$_3$ and CP$_4$ are independently a conjugated polymer segment or an oligomeric structure, wherein one or more of CP$_1$, CP$_2$, CP$_3$ and CP$_4$ are bandgap-lowering π-conjugated repeat units, and each n and each m are independently 0 or an integer from 1 to 10,000 and p is an integer from 1 to 100,000.

In some instances, the polymeric dye includes the following structure:

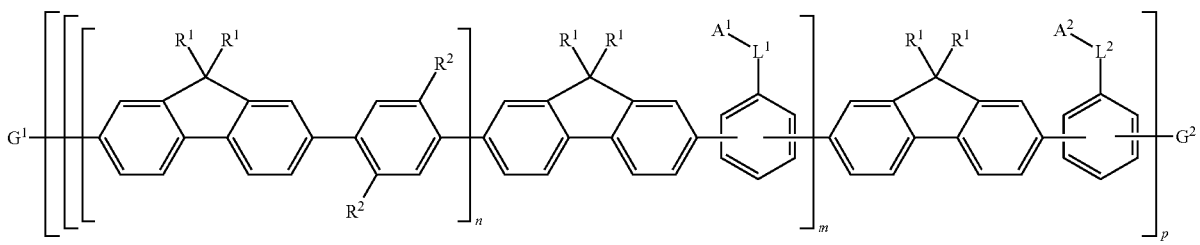

where each R$^1$ is independently a solubilizing group or a linker-dye; L$^1$ and L$^2$ are optional linkers; each R$^2$ is independently H or an aryl substituent; each A$^1$ and A$^2$ is independently H, an aryl substituent or a fluorophore; G$^1$and G$^2$ are each independently selected from the group consisting of a terminal group, a π-conjugated segment, a linker and a linked specific binding member; each n and each m are independently 0 or an integer from 1 to 10,000; and p is an integer from 1 to 100,000. Solubilizing groups of interest include alkyl, aryl and heterocycle groups further substituted with a hydrophilic group such as a polyethylglycol (e.g., a PEG of 2-20 units), an ammonium, a sulphonium, a phosphonium, and the like.

In some cases, the polymeric dye includes, as part of the polymeric backbone, a conjugated segment having one of the following structures:

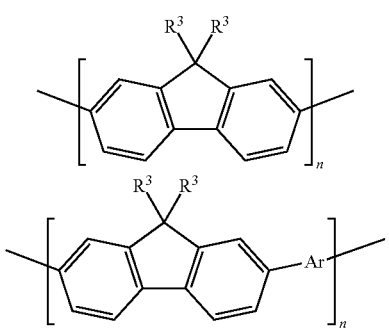

where each $R^3$ is independently an optionally substituted alkyl or aryl group; Ar is an optionally substituted aryl or heteroaryl group; and each n is an integer from 1 to 10,000. In certain embodiments, $R^3$ is an optionally substituted alkyl group. In certain embodiments, $R^3$ is an optionally substituted aryl group. In some cases, $R^3$ is substituted with a polyethyleneglycol, a dye, a chemoselective functional group or a specific binding moiety. In some cases, Ar is substituted with a polyethyleneglycol, a dye, a chemoselective functional group or a specific binding moiety.

In some instances, the polymeric dye includes the following structure:

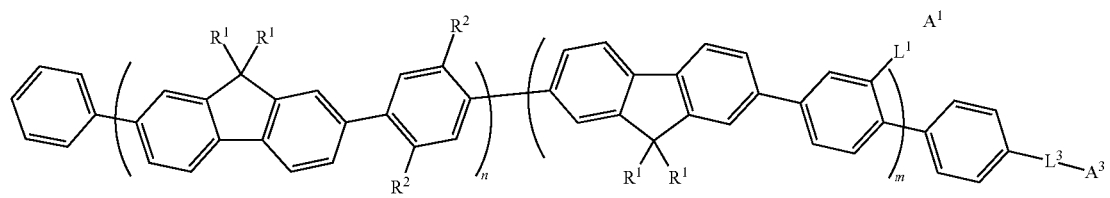

where each $R^1$ is independently a solubilizing group or a linker-dye group; each $R^2$ is independently H or an aryl substituent; each $L^1$ and $L^3$ are independently optional linkers; each $A^1$ and $A^3$ are independently H, a fluorophore, a functional group or a specific binding moiety (e.g., an antibody); and n and m are each independently 0 or an integer from 1 to 10,000, wherein n+m>1.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." *Cytometry Part A*, 81A (6), 456-466, 2012).

In some embodiments, the polymeric dye has an absorption curve between 280 nm and 475 nm. In certain embodiments, the polymeric dye has an absorption maximum (excitation maximum) in the range 280 nm and 475 nm. In some embodiments, the polymeric dye absorbs incident light having a wavelength in the range between 280 nm and 475 nm.

In some embodiments, the polymeric dye has an emission maximum wavelength ranging from 400 nm to 850 nm, such as 415 nm to 800 nm, where specific examples of emission maxima of interest include, but are not limited to: 421 nm, 510 nm, 570 nm, 602 nm, 650 nm, 711 nm and 786 nm. In some instances, the polymeric dye has an emission maximum wavelength in a range selected from the group consisting of 410 nm to 430 nm, 500 nm to 520 nm, 560 nm to 580 nm, 590 nm to 610 nm, 640 nm to 660 nm, 700 nm to 720 nm, and 775 nm to 795 nm. In certain embodiments, the polymeric dye has an emission maximum wavelength of 421 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, the polymeric dye has an emission maximum selected from the group consisting of 421 nm, 510 nm, 570 nm, 602 nm, 650 nm, 711 nm and 786 nm.

In some instances, the polymeric dye has an extinction coefficient of $1\times10^6$ cm$^{-1}$M$^{-1}$ or more, such as $2\times10^6$ cm$^{-1}$M$^{-1}$ or more, $2.5\times10^6$ cm$^{-1}$M$^{-1}$ or more, $3\times10^6$ cm$^{-1}$M$^{-1}$ or more, $4\times10^6$ cm$^{-1}$M$^{-1}$ or more, $5\times10^6$ cm$^{-1}$M$^{-1}$ or more, $6\times10^6$ cm$^{-1}$M$^{-1}$ or more, $7\times10^6$ cm$^{-1}$M$^{-1}$ or more, or $8\times10^6$ cm$^{-1}$M$^{-1}$ or more. In certain embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, or even more. In certain cases, the polymeric dye has a quantum yield of 0.1 or more. In certain cases, the polymeric dye has a quantum yield of 0.3 or more. In certain cases, the polymeric dye has a quantum yield of 0.5 or more. In some embodiments, the polymeric dye has an extinction coefficient of $1\times10^6$ or more and a quantum yield of 0.3 or more. In some embodiments, the polymeric dye has an extinction coefficient of $2\times10^6$ or more and a quantum yield of 0.5 or more.

Specific polymeric dyes that may be employed include, but are not limited to, BD Horizon Brilliant™ Dyes, such as BD Horizon Brilliant™ Violet Dyes (e.g., BV421, BV510, BV605, BV650, BV711, BV786); BD Horizon Brilliant™ Ultraviolet Dyes (e.g., BUV395, BUV496, BUV737, BUV805); and BD Horizon Brilliant™ Blue Dyes (e.g., BB515).

As summarized above, the MFI for the surface marker of interest is compared with a calibration plot obtained from a liposome calibration composition to quantify the EV surface marker(s) of interest. The calibration plot is a standard curve of the known number for the fluorophores (e.g., versus mean fluorescence intensity of the liposomes of the liposome calibration composition. More specifically, the calibration plot is a standard curve prepared from plotting expressed in the units known as Molecules of Equivalents Soluble Fluorochrome (MESF), the number of fluorophores vs. MFI for two or more distinct liposome subpopulations of the liposome calibration composition, where each distinct liposome subpopulation comprises a known amount of the fluorophore that differs from the amount of any other subpopulation in the liposome calibration composition. As reviewed below in greater detail, a given liposome calibration composition may include two or more distinct liposome subpopulations, such as three or more, four or more, five or more, including ten or more distinct liposome subpopulations. Accordingly, the calibration plot may be a line derived from values for 2 or more of the liposome subpopulations, such as three or more, four or more, five or more, including ten or more, and up to all of, the distinct liposome subpopulations in the calibration composition from which it is derived.

In some instances, the methods may include obtaining the calibration plot to which the surface marker MFI is compared. The calibration plot may be obtained by flow cytometrically analyzing the liposome calibration composition having the same fluorophore as the surface marker label to obtain MFI for the different liposome subpopulations of the calibration composition, and then plotting the observed MFI values vs. the known number of fluorophores (e.g., MESF) for each subpopulation.

Flow cytometry systems and methods for analyzing samples that may be employed in methods of the invention include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem. January;* 49(pt 1):17-28; Linden, et. al., *Semin Throm Hemost.* 2004 Oct.; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ II flow cytometer, BD Accuri™ flow cytometer, BD Biosciences FACSCelesta™ flow cytometer, BD Biosciences FACSLyric™ flow cytometer, BD Biosciences FACSVerse™ flow cytometer, BD Biosciences FACSymphony™ flow cytometer BD Biosciences LSRFortessa™ flow cytometer, BD Biosciences LSRFortess™ X-20 flow cytometer and BD Biosciences FACSCalibur™ ell sorter, a BD Biosciences FACSCount™ cell sorter, BD Biosciences FACSLyric™ cell sorter and BD Biosciences Via™ cell sorter BD Biosciences Influx™ cell sorter, BD Biosciences Jazz™ cell sorter, BD Biosciences Aria™ cell sorters and BD Biosciences FACSMelody™ cell sorter, or the like. In some embodiments, the subject particle sorting systems are flow cytometric systems, such those described in U.S. Pat. Nos. 9,952,076; 9,933,341; 9,726,527; 9,453,789; 9,200,334; 9,097,640; 9,095,494; 9,092,034; 8,975,595; 8,753,573; 8,233,146; 8,140,300; 7,544,326; 7,201,875; 7,129,505; 6,821,740; 6,813,017; 6,809,804; 6,372,506; 5,700,692; 5,643,796; 5,627,040; 5,620,842; 5,602,039; the disclosure of which are herein incorporated by reference in their entirety.

The MFI values may be obtained as described above, e.g., using FlowJo™ Software to process flow cytometrically obtained data, e.g., obtained using a flow cytometer as described above. In embodiments, the flow cytometrically obtained data for the liposome calibration composition is obtained using the same flow cytometer settings, e.g., fluorescence and compensation settings, as employed to obtain the EV surface marker MFI, e.g., the same voltage parameters for the photomultiplier of the flow cytometer, etc.

As reviewed above, the surface marker MFI for the labeled EV sample is compared with the calibration plot to obtain the number of fluorophores bound to the surface of EV vesicles of the EV sample, and thereby a quantitation of the EV surface marker of interest. In comparing the surface marker MFI to the calibration plot, any convenient protocol may be employed. For example, the surface marker MFI may be matched with the corresponding MFI of the calibration plot and the corresponding number of fluorophores (e.g., MESF) determined therefrom. An equation of the slope of the plot may be obtained and the surface marker MFI employed in the equation to solve for the number of fluorophores (e.g., MESF). The obtained number of fluorophores (e.g., MESF value) for the surface marker may be employed by itself as a quantitation value for the surface marker, or further employed to determine bound surface marker labels per EV (e.g., by accounting for ratios of fluorophore per specific binding members in a given surface marker label), and therefore surface markers per EV.

The methods as described herein can be employed to quantitate surface markers of a variety of different types of EVs. EVs for which surface markers may be quantitated using methods of the invention include, but are not limited to: micro-vesicles, exosomes, etc. In some instances, the extracellular vesicle has a diameter of 5μ or less, such as 1μ or less, where in some instances the extracellular vesicle has a diameter ranging from 30 to 2500 nm, such as 30 to 1000 nm. In some instances, the EV is an exosome (e.g., having a diameter ranging from 30 to 150 nm).

EV surface markers that may be quantitated using methods of the invention may vary. Surface markers of interest include, but are not limited to: ALCAM; CD166; ASGR1; BCAM; BSG; CD147; CD14; CD19; CD2; CD200; CD127; CD25; CD161; CD45RA; CD15S; CD4; CD127; CD15S; CD3; EpCAM; CD44; Her2/Neu; ACVR1B; ALK4; ACVR2A; ACVR2B; BMPR1A; BMPR2; CSF1R; MCSFR; CSF2RB; EGFR; EPHA2; EPHA4; EPHB2; EPHB4; ERBB2; androgen receptor; CAR; ER Alpha; ER Beta; ESRRA; ESRRB; ESRRG; FXR; Glucocorticoid Receptor; LXR-a; LXR-b; PPARA; PPARD; PPARG; PXR; SXR; Estrogen Receptor Beta; Progesterone Receptor; RARA; RARB; RARG; RORA; RXRA; RXRB; THRA; THRB; Vitamin D3 Receptor; AGER; APP; CLEC12A; MICL; CTLA4; FOLR1; FZD1; FRIZZLED-1; KLRB1A; LRPAP1; NCR3; NKP30; OLR1; PROCR; PTPN1; SOX9; SCARB2; TACSTD2; TREM1; TREM2; TREML1; and VDR.

Figure 2A:
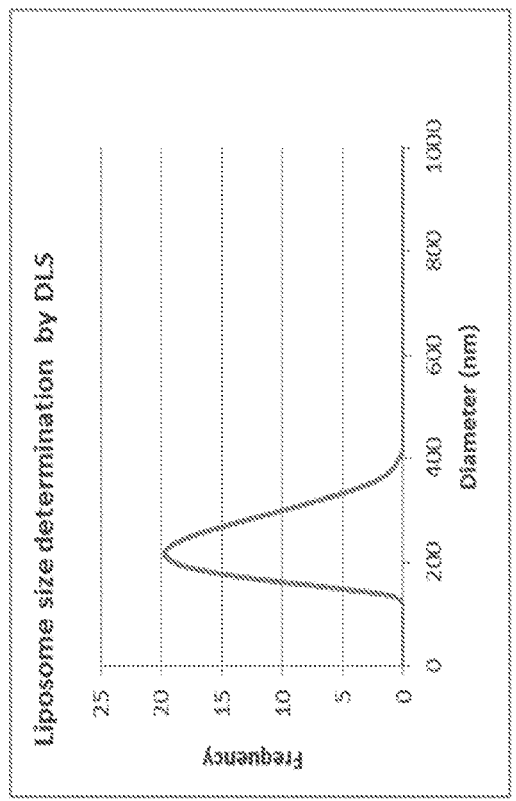
FIGS. 2A to 2C illustrate FITC Labeled liposomes analyzed by DLS and flow cytometry.

In some instances, the methods may further include employing the liposome calibration composition as a size calibrator for the EV particles. Since both liposomes and EVs are made of phospholipids, the Refractive Index (RI) of the liposome is substantially the same as that of EVs. Furthermore, since the diameter of labeled liposomes of the liposome calibration compositions ranges between 100-500 nm, which is the same range as EV particles, the labeled liposomes can be used as size estimation for EV particle diameter. Currently, polystyrene and silica beads are used as size calibrators, which have significantly different RI from a biological sample such as EVs. This difference in RI value introduces errors in size estimation of the EV particles. Liposomes are composed of phospholipid, cholesterol and fatty acid derivatives, such as 1-palmitoyl-2-myristoyl-sn-glycero-3-phosphocholine (PMPC), 1,2-dioleoyl-sn-glycero-3-phosphocholine ((DOPC), 1,2-dioleoyl-sn-glycero-3-phospho-L-serine (sodium salt) (DOPS), 1,2-dioleoyl-sn-glycero-3-phosphoethanolamine (DOPE). These constituents are the same chemical components that constitute the membrane of EV particles. Therefore, the refractive index of liposomes is identical to those of EV particles. In one embodiments, liposomes with an average diameter of 210 nm (e.g., as shown in FIG. 2A) are employed for all different liposome intensities, such that the size of the particles will remain constant and the average size of the labeled liposomes provides a size estimation reference for the EV particles.

Liposome Calibration Compositions

As reviewed above, methods of the invention employ liposome calibration compositions. Liposome calibration compositions are compositions comprising two or more distinct liposome subpopulations each comprising a known amount of a fluorophore that differs from the amount of any other subpopulation in the liposome calibration composition. As such, a given liposome calibration composition includes at least a first subpopulation of liposomes that includes a first known amount of a fluorophore, e.g., in terms of MESF, and a second subpopulation of liposomes that includes a second known amount of the same fluorophore, e.g., in terms of MESF, where the number of fluorophore molecules of the second subpopulation is different from the number of fluorophore of the first subpopulation. A given liposome calibration composition may include two or more distinct liposome subpopulations, such as three or more, four or more, five or more, including ten or more distinct liposome subpopulations.

The size of the liposomes of the liposome calibration composition may vary. In some cases, the liposomes have an average size (e.g., an average diameter) of 1000 nm or less, such as 900 nm or less, or 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 20 nm or less, or 15 nm or less, or 10 nm or less, or 5 nm or less, or 1 nm or less, where in some instances the size average size is 1 nm or more, such as 5 nm or more. In certain instances, the liposomes have an average size of 1000 nm or less. In certain instances, the liposomes have an average size of 800 nm or less. In certain instances, the liposomes have an average size of 500 nm or less. In certain instances, the liposomes have an average size of 400 nm or less. In certain instances, the liposomes have an average size of 300 nm or less. In certain instances, the liposomes have an average size of 250 nm or less. In certain instances, the liposomes have an average size of 200 nm or less. In certain instances, the liposomes have an average size of 100 nm or less. In certain instances, the liposomes have an average size of 50 nm or less. For example, the liposomes may include small unilamellar vesicles (SUVs), e.g., unilamellar vesicles having an average size of 100 nm or less, such as ranging from 10 nm to 100 nm. In some instances, the liposomes have a size ranging from 50 to 1000 nm, such as 100 to 500 nm.

In certain embodiments, the liposomes are uniform in size, such that they exhibit low polydispersity. "Dispersity" or "polydispersity" is a measure of the heterogeneity of sizes of particles in a mixture. In the context of liposomes, polydispersity can range from 0 to 1, where a polydispersity of 0 indicates a monodisperse population of liposomes (e.g., liposomes that have the same average size), and where a polydispersity of 1 indicates a heterogeneous mixture of liposomes. In some cases, the size of liposomes (and thus the polydispersity) can be determined by dynamic light scattering (DLS). In some cases, the polydispersity of the liposomes may be 0.1 or less. In some cases, the polydispersity of the liposomes may be 0.05 or less. In some cases, the polydispersity of the liposomes may be 0.01 or less. In certain instances, the polydispersity of the liposomes ranges from 0.01 to 0.5, such as 0.01 to 0.4, or 0.01 to 0.3, or 0.01 to 0.2, or 0.01 to 0.1. In other embodiments, the polydispersity of the liposomes ranges from 0.01 to 0.5, such as 0.01 to 0.5, or 0.01 to 0.4, or 0.01 to 0.3, or 0.01 to 0.2. In other embodiments, the polydispersity of the liposomes ranges from 0.01 to 0.5, such as 0.05 to 0.5, or 0.1 to 0.5, or 0.1 to 0.4, or 0.1 to 0.3. In other embodiments, the polydispersity of the liposomes ranges from 0.01 to 0.5, such as 0.05 to 0.5, or 0.1 to 0.5, or 0.2 to 0.5, or 0.2 to 0.4.

Liposomes useful in embodiments of the present disclosure are composed of lipids. In certain embodiments, the lipids are amphiphilic. Amphiphilic lipids may include a hydrophilic group and one or more lipophilic groups covalently bonded to the hydrophilic group. In some cases, the hydrophilic group is a charged group, such as an anionic group or a cationic group. In some instances, the hydrophilic group is an uncharged, polar group. In some embodiments, the hydrophilic group includes a charged group and a polar group. Examples of hydrophilic groups include, but are not limited to, phosphate, phosphocholine, phosphoglycerol, phosphoethanolamine, phosphoserine, phosphoinositol, ethylphosphophosphorylcholine, polyethyleneglycol, polyglycerol, sphingosine, phosphoshingosine, tri-nitrilotriacetic acid, melamine, glucosamine, trimethylamine, spermine, spermidine, and conjugated carboxylates, sulfates, boric acid, sulfonates, sulfates, carbohydrates, amino acids, and the like. In some cases, the hydrophilic group includes phosphocholine.

In certain embodiments, the lipophilic group includes an aliphatic chain, such as a saturated or unsaturated, linear or branched, substituted or unsubstituted aliphatic chain. For example, the lipophilic group may include an aliphatic chain of 2 to 40 carbon atoms in length, and may be saturated or unsaturated, linear or branched, substituted or unsubstituted. For instance, the lipophilic group may include a saturated or unsaturated, linear or branched, substituted or unsubstituted hydrocarbon chain having from 2 to 40 carbon atoms, such as from 4 to 30 carbon atoms, or from 4 to 25 carbon atoms, or from 6 to 24 carbon atoms, or from 10 to 20 carbon atoms. In certain cases, the lipophilic group includes a saturated or unsaturated, linear or branched hydrocarbon chain having 18 carbon atoms. In certain cases, the lipophilic group includes a saturated or unsaturated, linear or branched hydrocarbon chain having 16 carbon atoms.

Embodiments of the liposomes include liposomes having a known amount of a fluorophore stably associated therewith. The fluorophore of the liposomes of the calibration composition is the same as that of the surface marker label, where examples of suitable fluorophores are provided above. By "stably associated" is meant that a moiety is bound to or otherwise associated with another moiety or structure under standard conditions. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. In certain embodiments, the fluorophore is covalently bound to the liposome. For instance, as described above, lipids that comprise the liposome may include a hydrophilic group, which, in some cases may include an activated functional group that provides for a covalent attachment to the fluorophore, e.g., so that the fluorophore is conjugated to the liposome. Any convenient activated functional group useful in chemical synthesis may be used to covalently bond the detectable label to the hydrophilic group of a lipid, such as, but not limited to, amine, carboxyl, amide, hydroxy, azide, maleimide, bromoacetyl, 2-pyridyldithiol, haloalkyl, alkene, or propargyl, or the like.

The average number of fluorophores stably associated with liposomes of a given liposome subpopulation, e.g., in terms of MESF, may vary. Among any two liposome subpopulations in a given calibration composition, the average number of fluorophores differs.

The liposome calibration compositions employed in embodiments of the invention may be prepared using any convenient protocol. In some instances, the protocol includes preparing two or more distinct liposome subpopulations each comprising a known amount of a fluorophore; and combining the two or more distinct liposome subpopulations to produce the liposome calibration composition, wherein the known amount of fluorophore of each subpopulation differs from the amount of any other subpopulation in the liposome calibration composition.

The fluorophore comprising liposomes of each subpopulation may be prepared using any convenient protocol. In some instances, the protocol includes preparing an initial population of fluorophore comprising liposomes and then employing a liposome extrusion device to produce a subpopulation of liposomes from the initial population, e.g., as described in U.S. Pat. No. 10,556,216 the disclosure of which is herein incorporated by reference. Following preparation of a given fluorophore comprising subpopulation, the average number of fluorophores, e.g., in terms of MESF, for that subpopulation may be determined using any convenient protocol, such as a protocol employing Quantibrite™ heads (Becton Dickinson and Company), where additional details about such beads and protocols for employing the same may be found in U.S. Pat. Nos. 6,350,619; 7,738,094; and 8,248,597, the disclosures of each of which are herein incorporated by reference in their entirety.

Following preparation, the disparate fluorophore comprising liposome subpopulations, the liposome subpopulations are combined to the produce the liposome calibration composition. The number of liposomes among different subpopulations may be the same or different. The disparate liposome subpopulations may be combined to produce the liposome calibration composition using any convenient protocol, e.g., by combining the disparate populations into a single container and mixing.

Kits

Aspects of the disclosure also a liposome calibration composition, e.g., as described above, where the liposome calibration composition is present in a suitable container, e.g., a tube. The liposome calibration composition may be provided as a liquid composition or dried composition, including freeze dried composition, as desired. The kits may further include a surface marker label, e.g., as described above, where the fluorophore of the surface marker label is the same as that of the liposome calibration composition.

The kits may further include a liquid. For instance, the kit may include a buffer, such as a sample buffer, a wash buffer, an assay buffer, and the like. In some cases, the kit may include a liquid suitable for a suspension of liposomes. The kits may further include additional reagents, such as but not limited to, detectable labels (e.g., fluorescent labels, colorimetric labels, chemiluminescent labels, multicolor reagents, avidin-streptavidin associated detection reagents, radiolabels, gold particles, magnetic labels, etc.), and the like.

In certain embodiments, the kits may also include a calibration standard. For example, the kits may include a set of labelled beads, such as a set of standard fluorescently labelled beads. The calibration standard may be useful for determining the accuracy of the assay apparatus and for ensuring consistency between subsequent assays. For example, the calibration standard may be useful for determining the accuracy of a flow cytometer. In some cases, the calibration standard includes a labelled bead, such as a fluorescently labelled bead. The fluorescently labelled bead may be a standard fluorescently labeled bead that is typically used as a calibration standard. Examples of standard fluorescently labeled beads include, but are not limited to, fluorescently labelled microparticles or nanoparticles. In some cases, the fluorescently labeled beads are configured such that they remain suspended in the assay mixture and do not substantially settle or aggregate. In some embodiments, the fluorescently labeled beads include, but are not limited to, fluorescently labelled polystyrene beads, fluorescein beads, rhodamine beads, and other beads tagged with a fluorescent dye. Additional examples of fluorescently labeled beads are described in U.S. Pat. Nos. 6,350,619; 7,738,094; and 8,248,597, the disclosures of each of which are herein incorporated by reference in their entirety.

In addition, the kits may include packaging configured to hold various components. The packaging may be a sealed packaging, e.g., a water vapor-resistant container, optionally under an air-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.). The kits may further include a liquid container, e.g., as described above.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., flash memory), etc., on which the information has been recorded or stored. Yet another form that may be present is a website address which may be used via the Internet to access the information at a removed site. Any convenient form of instructions may be present in the kits.

Utility

The subject methods, devices and systems find use in applications where quantitation of an EV surface marker(s) is desired. Such applications include research, and diagnostic/therapeutic applications. For example, the methods may be employed in various research applications, e.g., to identify new and useful EV markers. In other instances, the methods may be employed in diagnostic/therapeutic applications, such as where the labeled EV sample is obtained from a living subject and employed to obtain a diagnosis for a condition, such as a disease condition of the subject. In such instances, the methods may further include treating the treating the subject for the disease condition based on the obtained diagnosis.

As can be appreciated from the disclosure provided above, embodiments of the present disclosure have a wide variety of applications. Accordingly, the examples presented herein are offered for illustration purposes and are not intended to be construed as a limitation on the embodiments of the present disclosure in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

A. Preparation of Liposome Compositions:
(1) Liposomes Decorated with Fluorescent Proteins Primary amine functional groups are incorporated into liposome membrane using of DSPE-PEG (2000) amine (1,2-distearoyl-sn-glycero-3-phosphoethanolamine-PEG2000-amine) as described in U.S. patent application Ser. No. 15/472,053, the disclosure of which is herein incorporated by reference. The resulting liposome containing primary amine functional groups on its surface is reacted with SPDP (N-Succinimidyl 3-(2-pyridyldithio) propionate). The SPDP-liposome is then treated with DTT to generate free sulfhydryl (—SH) groups on the surface of liposomes. The resulting sulfhydryl-liposome preparation is reacted with maleimide-derivatized green fluorescent protein (GFP), phycoerythrin (PE), allophycocyanine (APC), PerCp, and their tandem conjugates (PE-CF594, PE-Cy5, PE-Cy7, PE-H7, APC-R700, Percp-Cy5.5, etc.) to generate liposomes with variety of fluorescent proteins. The labeled liposomes are further purified by size exclusion column chromatography to provide purified preparation of labeled liposomes.

(2) Liposomes Decorated with Organic Fluorescent Dyes

Primary amine functional groups are incorporated in liposome membrane as described above in Example A(1). The liposome preparation with the primary amine groups on its surface is then reacted with variety of reactive fluorescent dyes containing NHS ester, Isothiocyanate or sulfonyl chloride. Typical examples of fluorescent dyes with reactive groups include a variety of Alexa-NHS ester dyes, Fluorescein, Rhodamine isothiocyanates, and Texas red sulfonyl chloride. The labeled liposome is purified from unreacted dyes by size exclusion column chromatography to provide a pure fraction of labeled liposomes. Alternatively, the liposomes can be labeled with fluorophores by direct incorporation of variety of commercially available fluorescent lipids or cholesterol into liposome membrane.

(3) Deposition of Functional Polymers on the Surface of Liposomes for Fluorescent Signal Enhancement Carboxyl functional groups are incorporated into the liposomes membrane using DSPE-PEG(2000) Carboxylic Acid (1,2-distearoyl-sn-glycero-3-phosphoethanolamine-N-[carboxy(polyethylene glycol)-2000]) during liposome preparation as described above in Examples A(1) and A(2), as well as U.S. Pat. No. 10,556,216, the disclosure of which is herein incorporated by reference. The carboxylated liposomes are reacted with a variety of aminated polymers such as polyallylamine, polvinylamine, polyethyleneimine, polylysine, aminated dextran, or chitosan in the presence of carbodiimide to create amide bonds between liposome carboxyl groups and aminated polymers. The resulting polymeric amine-liposomes structure is then reacted directly with variety of fluorescent dyes as described above in Examples A(1) and A(2). Alternatively, the above aminated polymers are labeled with fluorescent dyes prior to reaction with the liposome for covalent attachment to the surface of liposomes by the chemistries described above. Deposition of functional polymers on the surface of liposomes enhances the number of fluorescent dyes attached to the liposomes due to an increase in the number of amine functional groups, and hence the enhancement of the fluorescent intensities of liposome particles.

(4) Liposomes Modified by Click Chemistry

Liposomes are labeled with fluorescent dyes designed for Azido-Alkyne Cycloaddition or click chemistry. Liposome membranes are decorated with variety of alkyne or azide functional groups such as alkyne phospholipid, alkyne cholesterol, azido phosphocholine, azido diastearoyl-glycero-phosphoethanolamine, etc., as described earlier. The resulting functionalized liposomes are then reacted with fluorescent dyes designed for click chemistry carrying alkyne or azido functional groups. The fluorescent liposomes are further purified using size exclusion chromatography.

(5) Dyes Encapsulated Inside Liposomes

A variety of fluorescent proteins such as GFP, PE, APC, PercP and their corresponding tandem fluorophores (PE-CF594, PE-Cy5, PE-Cy7, PE-H7, APC-R700, Percp-Cy5.5, etc.) are encapsulated inside the liposome during preparation of the liposomes. Similarly, a variety of polymers labeled with fluorescent dyes such as those described in Example (3), and fluorescent conjugated polymers (or polymeric dyes) are directly encapsulated inside the liposomes.

(6) Preparation of Fluorescent Liposomes by Combination of the Chemistries Outlined Above A variety of fluorescent Liposomes using combination of both surface labeling and encapsulation of fluorophores inside the liposome are constructed to provide MESF liposome calibrators.

Figure 1B:
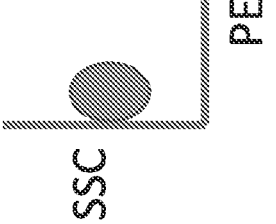
Figure 1B:
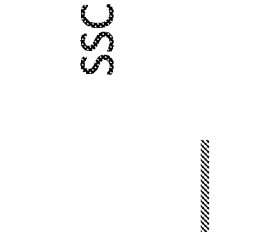
Figure 1B:
Figure 1B:
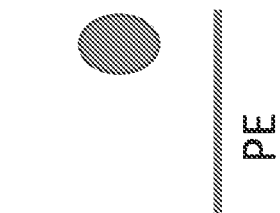
Figure 1B:
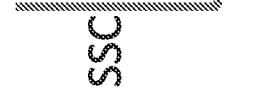
Figure 1C:
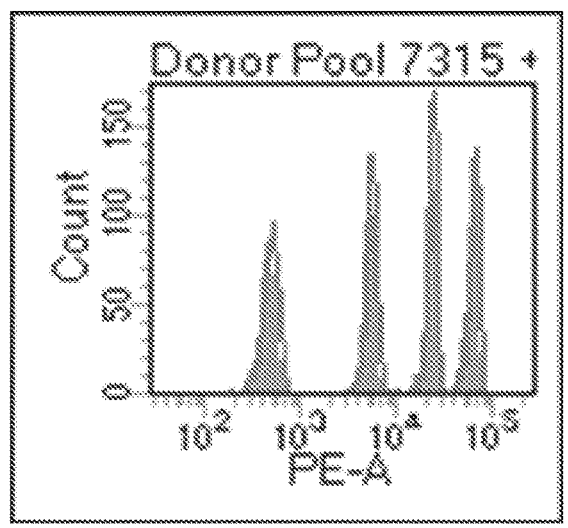
Figure 1C:
Figure 1C:
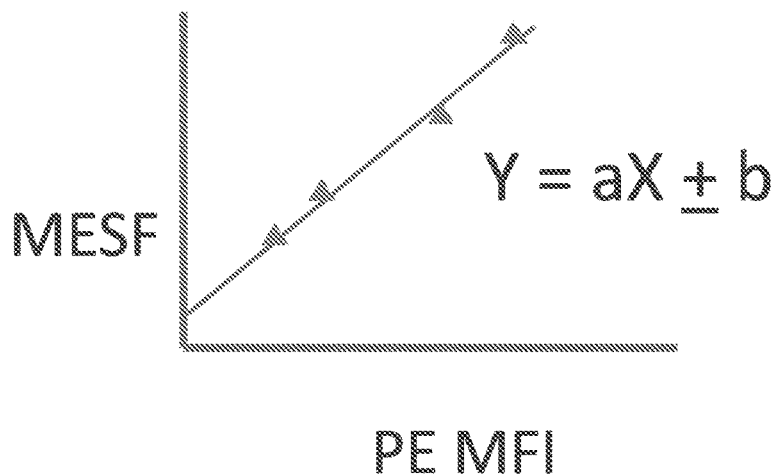

B. Characterization of Liposomes for the Number of Fluorophore Assignment:

Liposomes with different fluorescence intensities are generated using different concentrations of a reactive fluorescent dye such as FITC-NHS ester or Phycoerythrin-maleimide with a fixed number of liposome particles as described in Examples A1-4, above. An example of liposomes with various numbers of fluorophores bound to the liposomes is shown in FIG. 1A. Each labeled liposome is analyzed in a flow cytometer as shown in FIG. 1B. A plot of SSC (Side Scatter) vs PE fluorescent signal provides Mean Fluorescent Intensity (MFI) values for each liposome population of different labeling level. In order to assign the number of fluorophores to the liposomes with different MFI values, a set of fluorescent calibrator beads with known, number of fluorophore molecules such as PE-QuantiBRITE Beads, is analyzed in flow cytometer under the same PMT voltage and compensation setting for fluorescence channels as employed for the liposomes. A standard curve from these calibrator beads (a plot of MFI values vs their corresponding number of fluorophores) is used to calculate the number of fluorophore molecules for each liposome intensity. FIG. 1C shows the PE calibrator beads with their corresponding plots. Once the number of fluorophores is assigned to different intensities of liposomes, the liposomes are used as a calibrator set for determination of the number of fluorophore of an unknown EV sample.

Figure 2B:
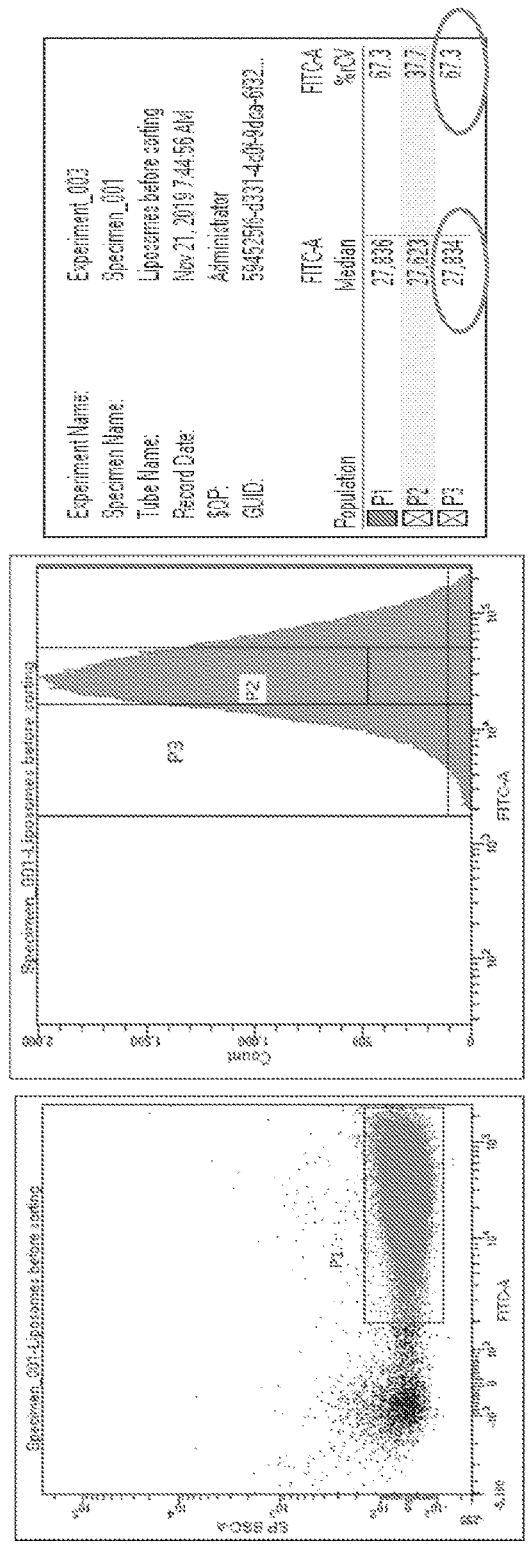
Figure 2C:
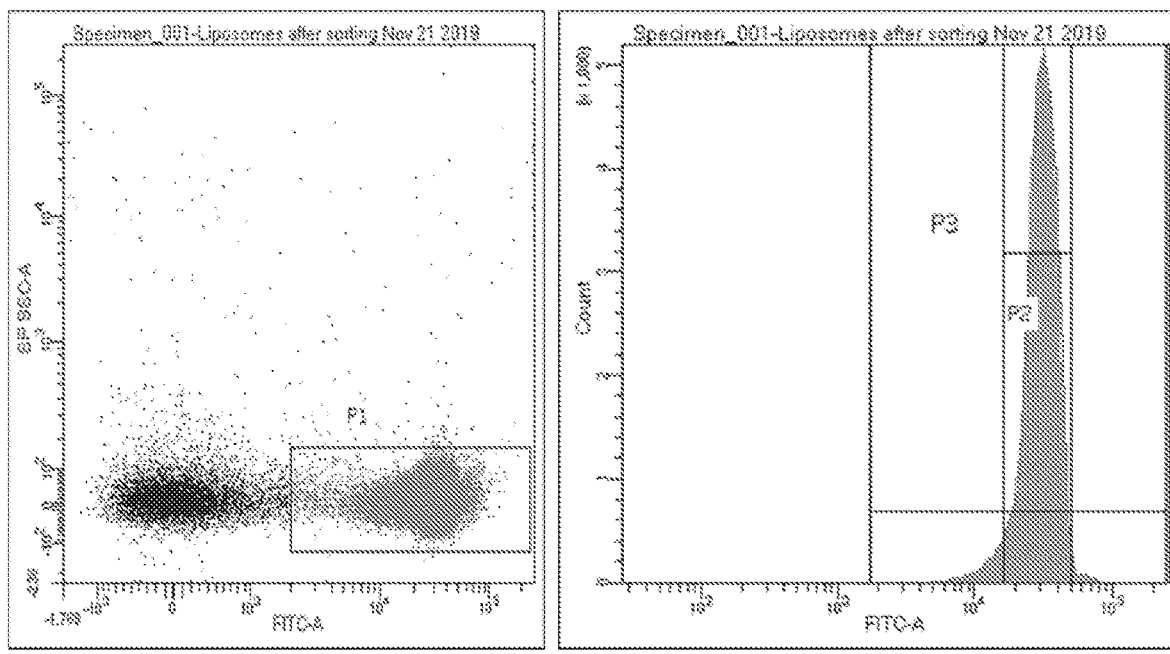
Figure 3A:
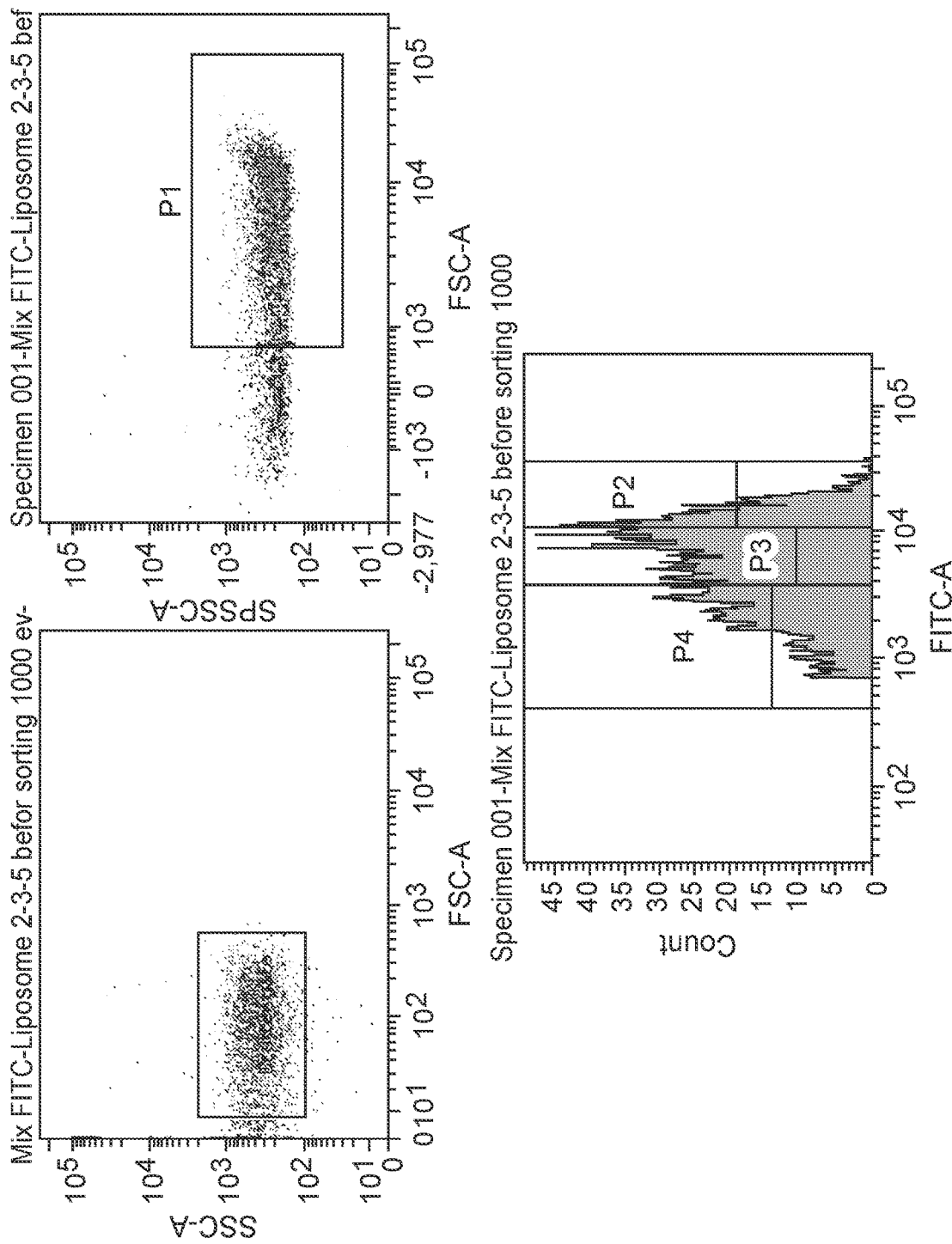
FIGS. 3A to 3B provide FITC labeled liposome calibrators.
Figure 3B:
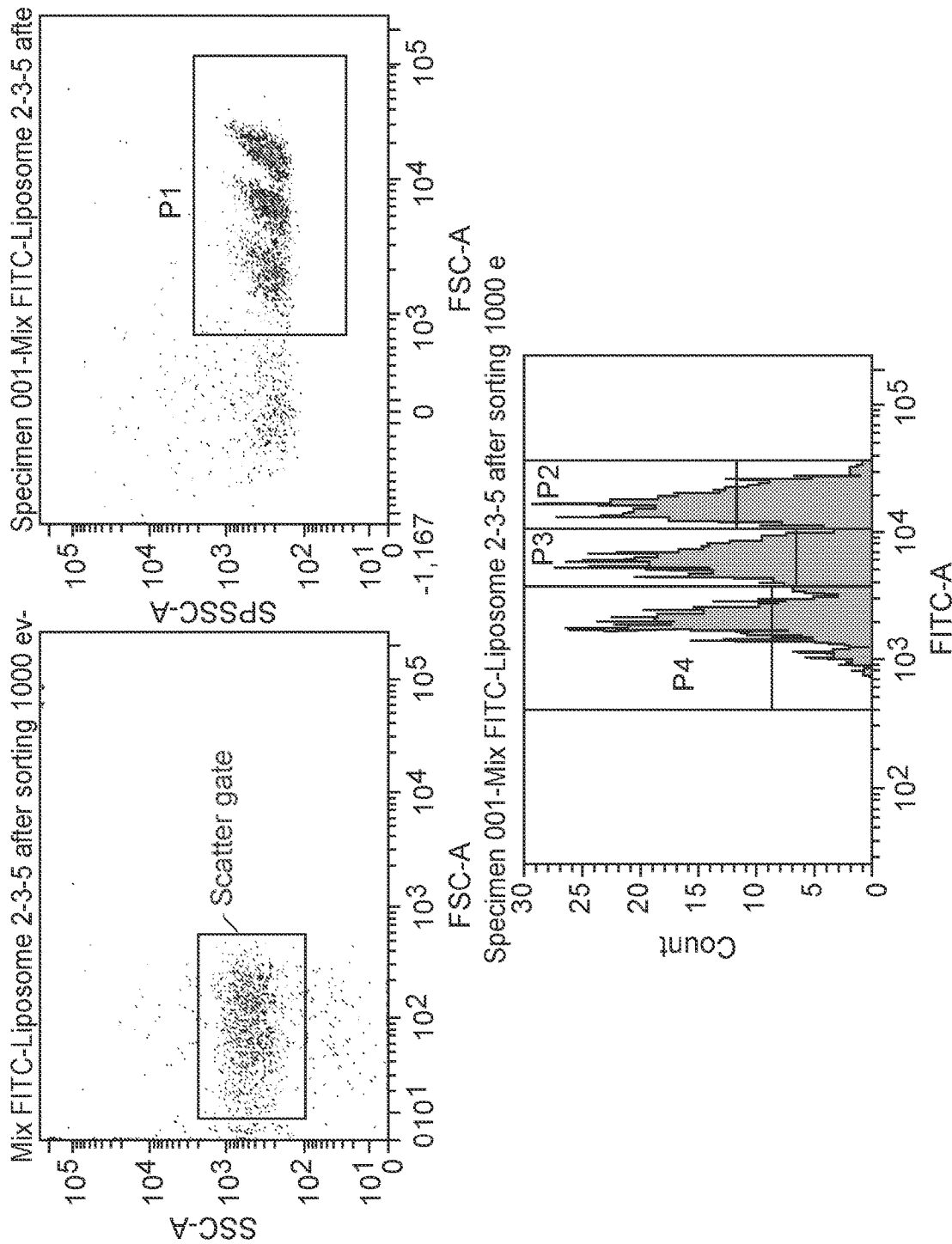

C. Characterization of Liposomes by Dynamic Light Scattering and Flow Cytometry:

Once a labeled liposome with a defined fluorescent intensity is prepared, the quality and the fluorescent intensity of the liposome are analyzed by two independent methods. The Dynamic Light Scattering (DLS) is used to provide information about the size distribution of the liposome population. FIG. 2A shows the size distribution of a FITC-labeled liposome preparation analyzed in DLS instrument. The diameter of the liposome population ranges from 150-400 nm with an average diameter of 210 nm. FIG. 2B shows the same liposome preparation analysis in flow cytometer in the form of dot plot (SSC vs FITC intensity) and histogram plot (Count vs FITC intensity). The dot plot shows the gated liposome population (P1) and the histogram plot shows the fluorescence intensity of the gated P1 liposome. As the data shows, the % CV of the histogram of the entire labeled liposome shown in the gate P3 is about 67.3% with MFI value of 27,834 (circled values in the table, respectively). This indicates that the MFI distribution of the liposome population is rather broad as indicated by a large value of its % CV (67%). In order to obtain liposome population with a smaller % CV of its MFI value, a narrower portion of the liposome population needs to be sorted in a flow cytometer. The gate P2 of the histogram in FIG. 2B shows the marked portion of the liposome population for sorting. FIG. 2C shows the data analysis for the sorted liposome population. As indicated by the circled values in the table, the % CV of the sorted liposomes has dramatically improved from 67% to 25.8% or by a factor of 2.6 fold, while the MFI values of the sorted population has remained virtually the same (30,061 FITC MFI) with no loss of FITC signal intensity. Therefore, by sorting the labeled liposomes of different intensities, one can generate series of liposomes with sufficiently narrow % CV in their MFI values such that they can be mixed in a single vial, and yet have well separated MFI histograms in a fluorescent channel. These well separated labeled liposomes with defined number of fluorophore molecules assigned to each intensity can serve as a calibrator set for quantitation of EV surface markers. FIGS. 3A to 3B provide results with FITC labeled liposome calibrators. FIG. 3A provides flow cytometry analysis of FITC-labeled liposomes on a BD FACS Aria Fusion before sorting. FIG. 3B provides FITC-labeled liposome calibrators generated after sorting in FACS Aria Fusion flow cytometer. The data demonstrates that liposome calibrators labeled with fluorophore can be generated.

Notwithstanding the appended claims, the disclosure is also defined by the following clauses:

1. A method of quantitating a surface marker on extra-cellular vesicles of a sample, the method comprising: comparing:
   (i) a mean fluorescence intensity of the surface marker (surface marker MFI) of a labeled extra-cellular vesicle (EV) sample, wherein the labeled EV sample has been labeled with a surface marker label comprising a specific binding member for the surface marker and a fluorophore; with
   (ii) a calibration plot obtained from a liposome calibration composition comprising two or more distinct liposome subpopulations each comprising a known amount of the fluorophore that differs from the amount of any other subpopulation in the liposome calibration composition;
to obtain the number of fluorophores bound to the surface of extracellular vesicles of the EV sample and quantify the surface marker on extra-cellular vesicles of the EV sample.

2. The method according to Clause 1, wherein the calibration plot comprises a plot of a known amount of the fluorophore for each of the distinct liposome subpopulations vs. the fluorescence intensity of the calibrating liposome composition.

3. The method according to any of Clauses 1 and 2, wherein the method further comprises obtaining the surface marker MFI of the labeled EV sample.

4. The method according to Clause 3, wherein the surface marker MFI of the labeled EV sample is obtained by flow cytometrically assaying the labeled EV sample.

5. The method according to Clause 4, wherein the method further comprises preparing the labeled EV sample.

6. The method according to Clause 5, wherein the specific binding member of the surface marker label comprises an antibody or binding fragment thereof.

7. The method according to any of the preceding clauses, wherein the method further comprises obtaining the calibration plot.

8. The method according to Clause 7, wherein the calibration plot is obtained by flow cytometrically assaying the liposome calibration composition.

9. The method according to Clause 8, wherein the liposome calibration composition is flow cytometrically assayed using the same flow cytometer at the same settings as that employed to flow cytometrically assay the labeled EV sample.

10. The method according Clause 9, wherein the same settings comprise the same voltage parameters for the photomultiplier of the flow cytometer.

11. The method according to any of the preceding clauses, wherein the fluorophore is selected from the group consisting of PE, PE-Cy7, APC, BV421, BV510 and BV605.

12. The method according to Clause 11, wherein the fluorophore is PE.

13. The method according to any of the preceding clauses, wherein the liposome calibration composition comprises three or more distinct subpopulations.

14. The method according to Clause 13, wherein the liposome calibration composition comprises four distinct subpopulations.

15. The method according to any of the preceding clauses, wherein the liposomes of the distinct subpopulations have a uniform size.

16. The method according to Clause 15, wherein the uniform size ranges from 100 to 500 nm.

17. The method according to any of the preceding clauses, wherein the method further comprises employing the liposome calibration composition as a size calibrator for the labeled EV sample.

18. The method according to any of the preceding clauses, wherein the labeled EV sample is prepared from an initial sample obtained from a living subject.

19. The method according to Clause 18, wherein the method further comprises obtaining for the subject a diagnosis of a disease condition based on the obtained quantitation.
20. The method according to Clause 19, wherein the method further comprises treating the subject for the disease condition based on the obtained diagnosis.
21. A liposome calibration composition comprising two or more distinct liposome subpopulations each comprising a known amount of a fluorophore that differs from the amount of any other subpopulation in the liposome calibration composition.
22. The liposome calibration composition according to Clause 21, wherein the liposome calibration composition comprises three or more distinct subpopulations.
23. The liposome calibration composition according to Clause 22, wherein the liposome calibration composition comprises four distinct subpopulations.
24. The liposome calibration composition according to any of Clauses 21 to 23, wherein the liposomes of the distinct subpopulations have a uniform size.
25. The liposome calibration composition according to Clause 24, wherein the uniform size ranges from 100 to 500 nm.
26. The liposome calibration composition according to any of Clauses 21 to 25, wherein the fluorophore is selected from the group consisting of PE, PE-Cy7, APC, BV421, BV510 and BV605.
27. The liposome calibration composition according to Clause 26, wherein the fluorophore is PE.
28. The liposome calibration composition according to any of Clauses 21 to 27, wherein the fluorophore is conjugated to the liposome.
29. A method of making a liposome calibration composition, the method comprising:
    (a) preparing two or more distinct liposome subpopulations each comprising a known amount of a fluorophore; and
    (b) combining the two or more distinct liposome subpopulations to produce the liposome calibration composition, wherein the known amount of fluorophore of each subpopulation differs from the amount of any other subpopulation in the liposome calibration composition.
30. The method according to Clause 29, wherein the liposome calibration composition comprises three or more distinct subpopulations.
31. The method according to Clause 30, wherein the liposome calibration composition comprises four distinct subpopulations.
32. The method according to any of Clauses 29 to 31, wherein the liposomes of the distinct subpopulations have a uniform size.
33. The method according to Clause 32, wherein the uniform size ranges from 100 to 500 nm.
34. The method according to any of Clauses 29 to 33, wherein the fluorophore is selected from the group consisting of PE, PE-Cy7, APC, BV421, BV510 and BV605.
35. The method according to Clause 34, wherein the fluorophore is PE.
36. The method according to any of Clauses 29 to 35, wherein the fluorophore is conjugated to the liposome.
37. A kit comprising:
    a liposome calibration composition comprising two or more distinct liposome subpopulations each comprising a known amount of a fluorophore that differs from the amount of any other subpopulation in the liposome calibration composition; and
    a container for the liposome calibration composition.
38. The kit according to Clause 37, wherein the liposome calibration composition comprises three or more distinct subpopulations.
39. The kit according to Clause 38, wherein the liposome calibration composition comprises four distinct subpopulations.
40. The kit according to any of Clauses 37 to 39, wherein the liposomes of the distinct subpopulations have a uniform size.
41. The kit according to Clause 40, wherein the uniform size ranges from 100 to 500 nm.
42. The kit composition according to any of Clauses 37 to 41, wherein the fluorophore is selected from the group consisting of PE, PE-Cy7, APC, BV421, BV510 and BV605.
43. The kit according to any of Clauses 37 to 42, wherein the kit further comprises a surface marker label comprising a specific binding member for the surface marker and the fluorophore.
44. The kit according to Clause 43, wherein the specific binding member comprises an antibody or binding fragment thereof.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc."

is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of quantitating a surface marker on extracellular vesicles of a sample, the method comprising:
   comparing:
   (i) a mean fluorescence intensity of the surface marker (surface marker MFI) of a labeled extra-cellular vesicle (EV) sample, wherein the labeled EV sample has been labeled with a surface marker label comprising a specific binding member for the surface marker and a fluorophore; with
   (ii) a calibration plot obtained from a liposome calibration composition comprising two or more distinct liposome subpopulations each comprising a known amount of the fluorophore that differs from the amount of any other subpopulation in the liposome calibration composition, wherein:
   the fluorophore is covalently bound to the surface of a liposome or encapsulated within a liposome, and;
   the calibration plot comprises a plot of the known amount of the fluorophore for each of the distinct liposome subpopulations vs. a fluorescence intensity for each of the distinct liposome subpopulations;
   to obtain a count of the fluorophores bound to the surface of extracellular vesicles of the EV sample and quantify the surface marker on extra-cellular vesicles of the EV sample.

2. The method according to claim 1, wherein the method further comprises obtaining the surface marker MFI of the labeled EV sample.

3. The method according to claim 2, wherein the surface marker MFI of the labeled EV sample is obtained by flow cytometrically assaying the labeled EV sample.

4. The method according to claim 3, wherein the method further comprises preparing the labeled EV sample.

5. The method according to claim 4, wherein the specific binding member of the surface marker label comprises an antibody or binding fragment thereof.

6. The method according to claim 1, wherein the method further comprises obtaining the calibration plot.

7. The method according to claim 6, wherein the calibration plot is obtained by flow cytometrically assaying the liposome calibration composition.

8. The method according to claim 7, wherein the EV sample is flow cytometrically assayed using a flow cytometer comprising flow cytometer settings, and the liposome calibration composition is flow cytometrically assayed using the same flow cytometer at the same flow cytometer settings as that employed to flow cytometrically assay the labeled EV sample.

9. The method according claim 8, wherein the flow cytometer settings comprise voltage parameters for hemphotomultiplier of the flow cytometer, and wherein the same voltage parameters for the photomultiplier of the flow cytometer are used to flow cytometrically assay the EV sample and the liposome calibration composition.

10. The method according to claim 1, wherein the liposomes of the distinct subpopulations have a uniform size.

11. The method according to claim 1, wherein the method further comprises employing the liposome calibration composition as a size calibrator for the labeled EV sample.

12. The method according to claim 1, wherein the labeled EV sample is prepared from an initial sample obtained from a living subject.

13. The method according to claim 12, wherein the method further comprises obtaining for the subject a diagnosis of a disease condition based on the obtained quantitation.

14. The method according to claim 13, wherein the method further comprises treating the subject for the disease condition based on the obtained diagnosis.

\* \* \* \* \*